United States Patent [19]

Webster

[11] 4,036,048
[45] July 19, 1977

[54] HARDNESS TESTING DEVICE

[76] Inventor: Robert A. Webster, 1044 20th St., Unit N, Santa Monica, Calif. 90403

[21] Appl. No.: 760,945

[22] Filed: Jan. 21, 1977

[51] Int. Cl.² .............................................. G01N 3/42
[52] U.S. Cl. ...................................................... 73/81
[58] Field of Search ............................. 73/81, 78, 82

[56] References Cited

U.S. PATENT DOCUMENTS

| | | | |
|---|---|---|---|
| 1,192,670 | 7/1916 | Moore et al. | 73/81 |
| 2,839,917 | 6/1958 | Webster | 73/81 |

Primary Examiner—James J. Gill
Assistant Examiner—Anthony V. Ciarlante
Attorney, Agent, or Firm—Pastoriza & Kelly

[57] ABSTRACT

A frame body has a base portion for supporting a specimen and an integrally extending arm portion above the base portion for guiding a penetrating probe. Force is applied to the probe to urge it against the specimen. A portion of the frame body is in the form of a leg extending horizontally in spaced relationship to the base portion of the frame to terminate adjacent to the specimen. Reaction of the frame to applied forces causes relative movement between the base portion and the horizontally extending leg indicative of "springing" of the frame. A first electrical circuit provides a first signal proportional to the load applied to the penetrating probe. A second electrical circuit provides a second signal responsive to relative movement of the penetrating probe and supporting arm and a third electrical circuit provides a third signal responsive to relative movement between the base portion of the frame and the extending leg. A further circuit receives the second and third signals and subtracts the third signal from the second signal to provide an output signal which accurately indicates the penetration of the penetrating probe into the specimen. Any "springing" movement of the frame as a consequence of loading which would introduce an error into the depth of penetration measurement is thus automatically compensated.

5 Claims, 3 Drawing Figures

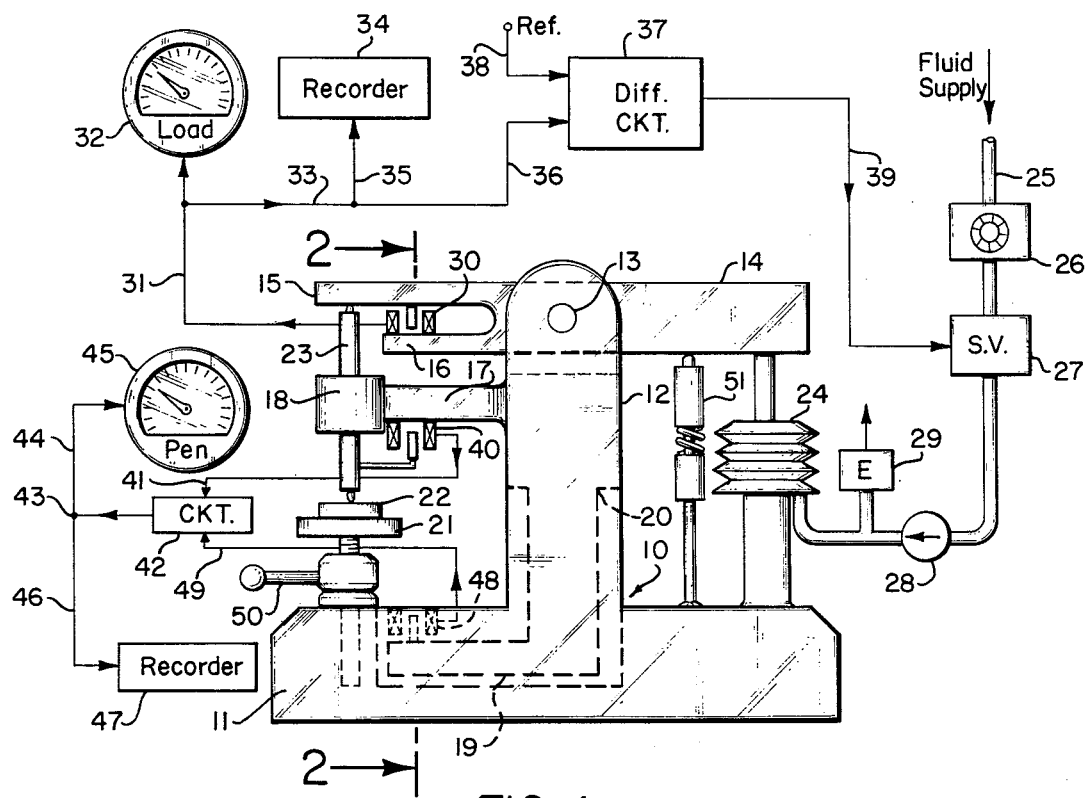
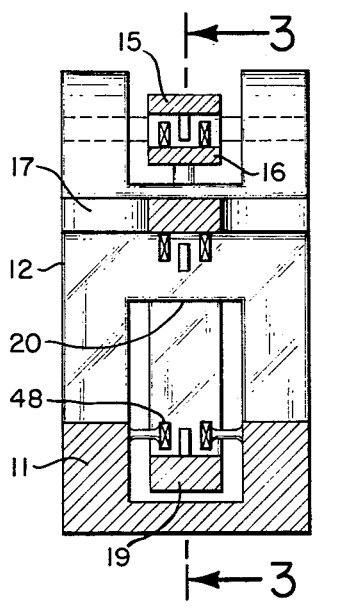
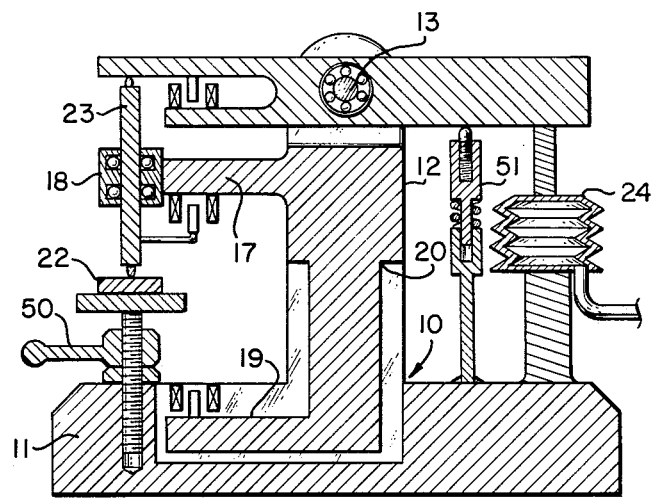

HARDNESS TESTING DEVICE

This invention relates generally to hardness testing devices and more particularly, to an improved hardness tester in which both loading and depth of penetration can be continuously indicated and recorded and wherein errors which might otherwise be introduced into the depth of penetration measurement are automatically compensated.

BACKGROUND OF THE INVENTION

Conventional hardness testing devices indicate the hardness of a metal or other material by the depth of penetration achieved by a penetrating probe under a given load or force. The depth serves as a numerical index to the hardness of the material. In certain instances, other physical dimensions of an impression, such as its diameter serve to indicate the hardness of the material. Alternatively, a numerical index to the hardness may be provided by measuring the load or force necessary to effect a desired depth of penetration.

Regardless of the type of device used, in calibrating the device for hardness, several readings or measurements are usually taken on a standard sample. Any variations between such readings are generally accountable to inaccuracies in the testing device itself rather than to inhomogeneities in the specimen. In other words, friction, initial impacts between the penetrator and specimen, and environmental vibrations transmitted through the testing device supports, all contribute towards the inability of the device to yield consistent readings.

As a result of the foregoing difficulties, hardness values for specific materials are given as a numerical range varying between the lowest and highest reading obtained on any one specimen. The numerical differences between the lower and higher numbers in the range are oftentimes sufficient to cause an overlapping of ranges for materials of similar hardness, whereby a differentiation between such materials is extremely difficult.

In my U.S. Pat. No. 2,839,917 issued June 24, 1958, I disclose an improved hardness testing device or machine which overcomes many of the problems contributing towards inaccuracy in readings. For example, many prior art hardness testers employ dead weights in providing a force or load on the penetrating probe. Clearly any outside vibrations causing motion of the hardness testing device itself will establish inertial forces through the dead weights which can impair the accuracy of penetration measurements. This specific problem is overcome by avoiding the use of dead weights and providing a force applying means such as a fluid operated bellows, all as described in my referred to U.S. patent.

Notwithstanding improved versions of hardness testers such as exemplified by my referred to patent, in all such devices which incorporate a frame body with spaced opposed portions between which forces are applied in urging the penetrator against a specimen, the frame body structure itself is subjected to stresses which can result in slight "springing" of the frame, thus changing the reference position of the specimen where it is supported on a portion of the frame caused to "give" or move. As a result, measurements of actual penetration of a probe under load urged against the specimen will be inaccurate since movement of the frame itself will result in movement of the specimen relative to the probe. Where very thin specimens are being tested, the depth of penetration is necessarily extremely slight, the same being measured in thousandths of an inch. It will be readily apparent that no matter how rigid the body frame is constructed, there still results a slight "give" or "springing" of the frame under loads particularly when extremely hard material is being tested.

BRIEF DESCRIPTION OF THE PRESENT INVENTION

With the foregoing considerations in mind, the present invention contemplates an improved hardness testing device having many of the advantageous features of the device set forth in my heretofore referred to patent but further including a unique means for compensating slight "springing" of the frame body under high loads, all to the end that extremely accurate measurements of the penetration distance of the probe under a given load can be realized.

More particularly, the present invention contemplates a frame body having a base portion for holding a specimen and an integral arm spaced from the base portion. A penetrating probe is supported on the arm for linear movement towards the specimen and appropriate force applying means mounted on the frame in turn exerts a force on the penetrating probe to urge it against the specimen. First electrical means responsive to the force applying means provides a first signal indicative of the force exerted on the penetrating probe. A second electrical means responsive to relative movement between the penetrating probe and the arm provides a second signal indicative of such movement. The frame body itself includes a leg portion integrally connected adjacent to the integral connection point of the arm and extending horizontally in spaced relationship to the base portion of the frame to terminate adjacent to the specimen. A third electrical means responsive to relative movement between the base portion of the frame supporting the specimen and the terminal end of this leg provides a third signal indicative of such movement.

Finally, an electrical circuit means is provided for subtracting the third signal from the second signal to provide an output signal which will be indicative of the actual penetration of the penetrating probe into the specimen. In other words, any "springing" of the base portion of the frame will result in generation of the third electrical signal and by subtracting this signal from the second signal, such "movement" is subtracted from the movement of the penetrating probe relative to the arm. The true penetration depth of the probe into the specimen is thus properly indicated while load is still applied to the penetrator.

BRIEF DESCRIPTION OF THE DRAWINGS

A better understanding of this invention as well as further features and advantages thereof will be had by referring to the accompanying drawings in which:

FIG. 1 is a side elevational view of the hardness testing device illustrating in schematic block form various electrical components associated therewith;

FIG. 2 is a cross section taken in the direction of the arrows 2—2 of FIG. 1; and, FIG. 3 is a further cross sectin taken in the direction of the arrows 3—3 of FIG. 2.

DETAILED DESCRIPTION OF THE PREFERRED EMBODIMENT

Referring first to FIG. 1, there is shown a frame body 10 having an horizontal base 11 and a central upwardly extending portion 12 carrying a pivot shaft 13.

A cross beam 14 is centrally pivoted to the pivot shaft 13 preferably by roller bearings. One end of the beam 14 constituting the left end as viewed in FIG. 1 to one side of the pivot shaft 13 is forked to define an upper bending beam portion 15 and a lower unstressed reference beam portion 16 extending in substantially parallel vertically spaced relationship. As shown, the frame body includes an arm 17 integrally secured to and horizontally extending from the central upwardly extending portion 12 beneath this reference beam 16, the arm 17 terminating in a vertical guide bearing 18.

In addition to the foregoing construction, and in accord with an important feature of this invention, the frame body 10 further includes a leg indicated in phantom lines in FIG. 1 at 19 secured to and horizontally extending from a lower portion of the central upwardly extending portion 12 adjacent to the horizontal base 11 and in spaced relationship thereto. In the particular construction illustrated, the spaced relationship is provided by cutting a cavity out from the frame body 10 all as will become clearer as the description proceeds. The integral connection of the leg 19 is preferably adjacent to the integral connection of the arm 17 in the upwardly extending portion 12 such as indicated at 20n phantom lines.

Adjacent to the terminal end of the leg 19 and supported on the horizontal base 11 of the frame body is a specimen platform 21 beneath the guide bearing 18 for supporting a specimen 22. A penetrating probe 23 is shown vertically passing through the guide bearing 18 with its upper end engaging the underside end portion of the bending beam 15 and its lower end engaging the specimen 22 on the platform.

Referring to the right-hand portion of the frame body 10, there is shown a force apply means in the form of an expandable bellows 24 positioned between the right end or other end of the cross beam on the other side of the pivot shaft 13 and the right-hand horizontal base portion of the frame body. A fluid inlet line 25 arranged to be connected to a fluid supply connects to the bellows 4 through a variable orifice needle valve 26 in the line 25 followed by a solenoid valve 27. The solenoid valve 27 is responsive to an electrical signal to close off fluid flow to the bellows. A check valve 28 is disposed in the line between the solenoid valve and bellows 24 to block back flow of fluid to the solenoid valve. Also shown is a manually operable exhaust valve 29 for relieving fluid pressure in the bellows 24.

Referring again to the left end of the cross beam 14, there is schematically illustrated a first electrical measuring mean 30 connected between the bending beam portion 15 and the reference beam portion 16 for providing a first signal reponsive to movement of the bending beam relative to the reference beam. This signal is passed along a line 31 to a first indicating means in the form of a load measuring meter 32 which will provide an indication of the force applied to the probe by the bending beam portion 15 resulting from application of force by the force applying bellows 24 when the same is expanded by fluid from the fluid supply.

The first signal on the line 31 is tapped off by branch line 33 and passed to a recorder 34 though a further branch line 35 as indicated. Recorder 34 will provide a permanent record, if desired, of the load forces applied to the penetrator.

As also illustrated in the upper portion of FIG. 1, the first signal on the branch line 33 is passed through line 36 to the first input of a differential circuit 37. The second input of this differential circuit is shown at 38 for receiving a given reference signal. The differential circuit 37 is designed to provide an output signal only when the magnitude of the signal on the first input 36 exceeds the reference signal on the second input 38. This output signal is passed on line 39 to the solenoid valve 27 and will close this valve and thus stop fluid flow to the bellows 24.

With the foregoing arrangement, it will be evident that different loads can be automatically established by appropriate given reference signals applied at the second input 38 to the differential circuit 37. In other words, assuming that the first signal increases linearly with increased loading, when the magnitude of the signal passes the magnitude of the input reference signal, the output signal on line 39 will be generated to immediately close the solenoid valve 27 and thus hold the specific value of loading on the penetrator 23.

Referring now to the arm portion 17 and guide bearing 18, it will be noted that a similar second electrical measuring means 40 is connected between the arm and the penetrating probe 23 for providing a second signal responsive to movement of the probe relative to the arm 17 and guide bearing 18. This second signal passes along line 41 to a first input of an electrical circuit means 42. The output of the circuit means 42 passes to a junction 43 and line 44 to a second indicating means in the form of a penetration meter 45. The output signal at junction 43 also passes through branch lead 46 to a recorder 47.

If it could be assumed that the platform 21 and specimen 22 were held by the frame body absolutely stationary with respect to the arm 17, the second signal on line 41 to the electrical circuit means 42 would be an accurate indication of the penetration of the probe 23 into the specimen 22. However, because of the relatively large loading involved, particularly when hard specimens are being tested, there is a tendency for the horizontal base portion 11 of the frame body to "give" or "spring" slightly under the large forces. In other words, the lower horizontal base portion 11 of the frame would tend to bow as a consequence of the forces existing between the opposite ends of the cross beam 14 and the left and right end portions of the base. This "bowing" or "springing" of the frame will result in a slight downward movement of the specimen platform and specimen itself relative to the probe 23 so that the second signal provided on the line 41 is really not an accurate indication of the depth of penetration of the probe into the specimen.

The foregoing problem is overcome in the present invention by the provision of the horizontally extending leg 19 described heretofore. In this respect, there is provided as indicated in the phantom lines a third electrical measuring means 48 connected between the extending end portion of the leg 19 and the horizontal base 11 for providing a third signal responsive to movement of the horizontal base relative to the leg. Bowing or "springing" of the base portion of the frame under loading results in this movement, the leg itself in view of its horizontal extension in spaced relationship to the base portion effectively defining a "zero" reference.

The third signal is passed on line 49 to a second input of the electrical circuit means 42. The electrical circuit means 42 functions to simply subtract from the second signal the third signal so that the actual occurring at the junction 43 will represent the actual penetration of the probe into the specimen. In other words, any downward movement of the specimen as a result of bowing or "springing" of the base portion of the frame under load is subtracted from the movement recorded by the second signal between the probe 23 and arm 17. Essentially, the arm 17 and leg 19 integrally interconnected at 20 within the upwardly extending portion 12 are not subject to the loading forces and thus constitue appropriate reference points.

The device is completed by the provision of a manually rotatable fixture 50 for raising or lowering the platform 21 carrying the specimen 22 so that when a test is to be made, the specimen 22 may be brought up into initial contact with the lower end of the penetrating probe 23. Spring loaded stop 51 serves to place a minor load on the cross beam to remove any play or slack in this initial contact.

In FIG. 2, the manner of constructing the leg 19 relative to the horizontal base portion of the frame 11 will be evident. Thus, a cavity portion is essentially provided in the overall frame body so that the leg itself can extend in horizontal spaced relationship thereto and thus not be subjected to the "springing" action. FIG. 2 also illustrates clearly the third electrical measuring means 48.

In FIG. 3, the roller bearings for the pivot shaft 13 are shown in schematic cross section. Further, the guide bearing 18 is illustrated as comprised of appropriate ball bearings for guiding the probe 23 in a vercial direction. Finally, FIG. 3 illustrates in the solid line cross sectional portion the phantom line configuration for the leg 19, the integral relationship of this leg with respect to the arm 17 being evident.

The first, second and third electrical measuring means 30, 40 and 48 respectively, may each constitute simple linear variable differential transformers referred to in the art as "LVDT" manufactured by Schaevitz. The devices essentially comprise three coils with a center core movable relative to the coils, the output signals being a function of the position of the core relative to the coils.

The variable orifice needle valve 26 described in FIG. 1 enables accurate metering of the fluid supply to the bellows 24. Thus, the rate of force application can be manually adjusted by means of this needle valve 26. The actual fluid supply itself may constitute the normal compressed air supply available in most machine shops or may constitute hydraulic fluid provided from an appropriate pump or any other equivalent fluid source.

OPERATION

The operation of the hardness testing device of this invention will be readily apparent from the foregoing description. Initially, the specimen to be tested such as indicated at 22 in FIG. 1 is placed on the platform 21 and the manual fixture 50 appropriately rotated to raise the platform 21 and specimen until the lower end of the penetrating probe 23 engages the top surface of the specimen. Zero adjustments of all of the three electrical measuring means 30, 40 and 48 are effected by any conventional zeroing means such as adjustable mechanical mounting of the devices so that movement of the probe relative to the coils can be effected independently of the other components to zero the devices under no load conditions.

A desired given load is automatically established by providing a given value for the reference signal applied to the differential circuit 37 on the second input 38. Pressure may now be applied to the bellows 24 through the variable needle valve 26, solenoid valve 27 and check valve 28, the exhaust valve 29 being closed.

As the bellows 24 expands, it will exert an upward force on the right end of the cross beam 14 thereby causing the left bending beam portion 15 to exert a downward force on the penetrator 23 and force the lower end of the penetrator into the specimen 22.

The applied force results in bending of the beam portion 15 thereby generating the first signal referred to in line 31 which signal is continuously indicated by the meter 32 and automatically recorded by the recorder 34.

When the magnitude of this first signal exceeds the reference signal on the second input 38, an output signal is automatically generated by the differential circuit 37 to actuate the solenoid valve 27 and close off further fluid flow to the bellows 24. Thus, a given known load is applied to the penetrator 23.

The second indicating means in the form of the penetration meter 45 in turn will automatically continuously indicate the exact degree of depth penetration by the probe as a consequence of the output signal from the electrical circuit means 42. As described heretofore, this output signal constitutes the difference between the second signal from the second electrical measuring means 40 and the third signal from the third electrical measuring means 48. Any movement of the base portion of the frame body as a result of the large loading forces is thus automatically compensated for in the readings of the penetration meter 45 and the recording of these readings by the recorder 47 accurately depict the actual penetration of the probe 23 into the specimen.

Advantages accruing from the hardness testing device of this invention are numerous. Essentially, there is no friction from moving parts. Further there is no impact effect upon loading or unloading because of the careful control provided by the needle valve and static balancing of the cross beam.

As a consequence of the roller bearing arrangement of the cross beam on the pivot shaft, there is no hysteresis resulting from loading or unloading or from the environmental components.

By the provision of the recorders, and also by the provision of a fluid supply line for the force applying means, operation is possible from a remote location.

Most importantly, any "springing" of the frame body is compensated as described.

From all of the foregoing, it will thus be evident that the present invention has provided a greatly improved hardness testing device.

What is claimed is:
1. A hardness testing device including, in combination:
   a. A frame body having a base portion for holding a specimen and an integral arm spaced from said base portion;
   b. a penetrating probe supported on said arm for linear movement towards said specimen;
   c. force applying means mounted on said frame body for exerting a force on said penetrating probe to urge it against said specimen;

d. first electrical means responsive to said force applying means to provide a first signal indicative of the force exerted on said penetrating probe;

e. second electrical means responsive to relative movement between said penetrating probe and said arm for providing a second signal indicative of said movement;

f. said frame body having a leg portion integrally connected thereto adjacent to the integral connection point of said arm and extending horizontally in spaced relationship to the base portion of said frame body to terminate adjacent to said specimen;

g. third electrical means responsive to relative movement between said base portion of said frame body supporting said specimen and the terminal end of said leg to provide a third signal indicative of said relative movement; and, h. electrical circuit means subtracting said third signal from said second signal to provide an output signal indicative of the penetration of said penetrating probe into said specimen.

2. A hardness testing device according to claim 1, in which said force applying means includes a cross beam pivoted to said body, one end portion of said cross beam engaging said penetrating probe; and a fluid operated bellows positioned between the other end portion of said cross beam and a horizontal portion of said frame body for exerting a force thereon in response to fluid pressure.

3. A hardness testing device including, in combination:

a. a frame body having an horizontal base and a central upwardly extending portion carrying a pivot shaft;

b. a cross beam centrally pivoted to said pivot shaft, one end of said beam on one side of said pivot shaft being forked to define an upper bending beam portion and a lower reference beam portion extending in substantially parallel vertically spaced relationship;

c. said frame body including an arm integrally secured to and horizontally extending from said central upwardly extending portion beneath said reference beam, said arm terminating in a vertical guide bearing;

d. said frame body including a leg secured to and horizontally extending from a lower portion of said central upwardly extending portion adjacent to said horizontal base in spaced relationship thereto;

e. A specimen platform supported on said horizontal base of said frame body beneath said guide bearing;

f. a penetrating probe vertically movable in said guide bearing with its upper end engaging the underside end portion of said bending beam and its lower end engaging a specimen receivable on said platform;

g. force applying means between the other end of said cross beam on the other side of said pivot shaft and said horizontal base;

h. first electrical measuring means connected between said bending beam portion and said reference beam portion of said cross beam providing a first signal responsive to movement of said bending beam relative to said reference beam;

i. second electrical measuring means connected between said penetrating probe and said arm for providing a second signal responsive to movement of said probe relative to said vertical guide bearing;

j. third electrical measuring means connected between the extending end portion of said leg and said horizontal base for providing a third signal responsive to movement of said horizontal base relative to said leg;

k. first indicating means responsive to said first signal to provide an indication of the force applied to said probe resulting from application of force by said force applying means;

l. circuit means subtracting said third signal from said second signal; and m. second indicating means connected to said circuit means and responsive to an output signal from said circuit means constituting the difference between said second signal and third signal to provide an indication of the penetration of said penetrating probe into said specimen.

4. A hardness testing device according to claim 3, in which said force applying means includes an expandable bellows; a fluid inlet line connected to said bellows for passing fluid thereto from a fluid supply source; a variable orifice needle valve in said line for controlling the rate of fluid admitted into said line to said bellows; a solenoid operated valve in said line following said needle valve responsive to an electrical signal to close off the flow through said line; and a check valve in said line following said solenoid valve to block back flow from said bellows to said solenoid valve; a differential circuit having a first input connected to said first electrical measuring means, a second input for receiving a given reference signal and an output connected to said solenoid valve for providing an electrical output signal to said valve for closing the same when the generated signal from said first electrical measuring means obtains a magnitude greater than said reference signal, whereby the loading applied to said cross beam by said bellows can be established at desired values in accord with given values of said reference signal.

5. A hardness testing device according to claim 4, including a first recorder connected to receive and record said first signal from said first electrical measuring means and a second recorder connected to receive and record the output signal from said circuit means connecting to said said second indicating means.

* * * * *